(12) United States Patent
Ruzafa et al.

(10) Patent No.: US 6,747,057 B2
(45) Date of Patent: Jun. 8, 2004

(54) COMPOUNDS AND THEIR THERAPEUTIC USE

(75) Inventors: Santiago Conde Ruzafa, Madrid (ES); Ana Martinez Gil, Madrid (ES); Daniel Ignacio Perez Fernandez, Madrid (ES); Maria Concepcion Perez Martin, Madrid (ES); Francisco Jose Moreno Munoz, Madrid (ES); Francisco Wandosell Jurado, Madrid (ES)

(73) Assignees: Consejo Superior de Investigaciones Cientificas, Madrid (ES); Universidad Autonoma de Matrid (UAM), Madrid (ES)

( * ) Notice: Subject to any disclaimer, the term of this patent is extended or adjusted under 35 U.S.C. 154(b) by 0 days.

(21) Appl. No.: 10/327,167

(22) Filed: Dec. 20, 2002

(65) Prior Publication Data

US 2003/0199508 A1 Oct. 23, 2003

(30) Foreign Application Priority Data

Dec. 21, 2001 (GB) .............................. 0130736
Jan. 24, 2002 (GB) .............................. 0201615

(51) Int. Cl.[7] ...................... A61K 31/38; C07D 333/22
(52) U.S. Cl. ...................... 514/446; 514/448; 549/70; 549/73
(58) Field of Search ................... 514/446, 448; 549/70, 73

(56) References Cited

FOREIGN PATENT DOCUMENTS

WO     WO 96/40982     12/1996

OTHER PUBLICATIONS

Jehan F. Bagli et al., "Thiophene Isosters of Phenylethanolamines", *Canadian Journal of Chemistry*, vol. 53, pp. 2598–2607 (1975).
Charles F. Barfknecht et al., "Nonclassical Nicotine Antagonists", *Journal of Medicinal Chemistry*, vol. 18, No. 10, pp. 1161–1164 (Oct., 1975).
Jose Barluenga et al., "Simple and Unambiguous Synthesis of α, α–, and α, α'—Dihalogeno Ketones[1]", *Royal Society of Chemistry Perkin Transactions 1*, vol., pp. 297–300 (Feb., 1991).
Belenkii et al., "Influence of the Nature of the Reactants and the Reaction Conditions on Friedel–Crafts Acylation I. Relative Activities of Alkanoyl and α–Halogenoalkanoyl Chlorides in the Friedel–Crafts Reaction", *Journal of Organic Chemistry of the USSR*, vol. 6, No. 12, pp. 2531–2536 (Dec., 1970).
Ana Castro et al., "Inhibition of tau phosphorylation: a new therapeutic strategy for the treatment of Alzheimer's disease and other neurodegenerative disorders", *Expert Opinion on Therapeutic Patents*, vol. 10, pp. 1519–1527 (2000).
S. Conde et al., "β–Adrenoceptor Blocking Activity of Halogenated Thienylethanolamie Derivatives", *Journal of Medicinal Chemistry*, vol. 20, No. 7, pp. 970–974 (1977).
M.J. del Agua et al., "Bromothiophene Reactions. I. Friedel–Crafts Acylation", *Journal of Heterocyclic Chemistry*, vol. 18, pp. 1345–1347 (1981).
Zhenjun Diwu et al., "A Facile Protocol for the Convenient Preparation of Amino–substituted α–Bromo– and α, α–Dibromo Arylmethylketones", *Tetrahedron Letters*, vol. 39, No. 28, pp. 4987–4990 (1998).
William S. Emerson et al., "2–Vinylthiophenes", *Journal of Organic Chemistry*, vol. 13, pp. 729–734 (1948).

(List continued on next page.)

*Primary Examiner*—Deborah C. Lambkin
(74) *Attorney, Agent, or Firm*—Fish & Richardson P.C.

(57) ABSTRACT

Compounds of formula I:

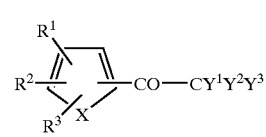

[wherein:

X represents —CH=CH—, —CH=CR—, —CR=CR—, —CO—, —O—, —NH—, —NR—, S—, —SO—, —SO$_2$—, —CH=N—, —CR=N—, —CH=N(O)—, —CR=N(O)— or any other atom or group of atoms capable of forming a 5— or 6-membered heterocyclic ring;

$Y^1$, $Y^2$ and $Y^3$ independently represent hydrogen or halogen;

$R^1$, $R^2$ and $R^3$ are independently represent hydrogen, halogen, hydrocarbyl (—R), hydroxyl (—OH), hydrocarbyloxy (—O—R), mercapto (—SH), hydrocarbylthio (—S—R), hydrocarbylsulfinyl (—SO—R), hydrocarbylsulfonyl (—SO$_2$—R), nitro (—NO$_2$), amino (—NH$_2$), hydrocarbylamino (—NHR), bis (hydrocarbyl)amino (—NR$_2$), hydrocarbylcarbonylamino (—NH—CO—R), cyano (—CN), carbamoyl (—CONH$_2$), hydrocarbylcarbarnoyl (—CONHR), bis (hydrocarbyl)carbamoyl (—CONR$_2$), carboxyl (—CO$_2$H), hydrocarbyloxycarbonyl (—CO$_2$R), formyl (—CHO), hydrocarbylcarbonyl (—COR), hydrocarbylcarbonyloxy (—OCOR), optionally substituted heteroaryl or optionally substituted heterocyclic; and the hydrocarbyl group R is a straight or branched chain hydrocarbyl group selected from alkyl, alkenyl, alkynyl, aryl, aralkyl, aralkenyl and aralkynyl, which may optionally be substituted by one or more substituents, selected from those defined above in relation to R1, R2 and R3]; are of use in the manufacture of a medicament for the treatment including prophylaxis of disease mediated by the activation of GSK-3.

16 Claims, No Drawings

Ewa Hellström–Lindahl, "Modulation of β–amyloid precursor protein processing and tau phosphorylation by acetylcholine receptors", *European Journal of Pharmacology*, vol. 393, pp. 255–263 (2000).

Bret E. Huff et al., "Synthetic Approaches to Benzofuran Containing Insulin Sensitivity Enhancer Compounds for Treatment of Type II Diabetes", *Heterocylces*, vol. 45, No. 7, pp. 1363–1384 (1997).

Khalid Iqbal et al., "Tau Phosphatases", *Brain Microtubule Associated Proteins Modifications in Disease*, Chapter 7, pp. 95–111 (1997).

Yasuji Izawa, "Photoinduced Alcoholysis of α,α,α–Tribromoacetophenone to Benzoylforate", *Bull. Chem. Soc. Japan*, vol. 56, No. 5, pp. 1490–1496 (1983).

J.J. Klingenberg et al., "β–Bromomandelic Acid (Mandelic acid, p–bromo)", *Organic Synthesis*, vol. 4, pp. 110–113 (1963).

Andrew J. Larner, "Tau protein as a therapeutic target in Alzheimer's disease and other neurodegenerative disorders", *Expert Opinion on Therapeutic Patents*, vol. 9, pp. 1359–1370 (1999).

G. Levi et al, "Autoradiographic Localization and Depolarization–Induced Release of Acidic Amino Acids in Differentiating Cerebellar Granule Cell Cultures", *Brain Research*, vol. 290, pp. 77–86 (1984).

Shulamit Magen et al., "Novel Bromination Reagents[1]. Hexabromocyclopentadiene: Bromination of Activated Saturated Sites", *Tetrahedron Letters*, vol. 25, No. 31, pp. 3369–3372 (1984).

Juzo Nakayama et al., "Preparation of an α, β–Type of Ter–and Septithiophenes", *Heterocycles*, vol. 26, No. 10, pp. 2599–2602 (1987).

Masaru Ogata et al., "Synthesis and Antifungal Activity of a Series of Novel 1,2–Disubstituted Propenones", *Journal of Medicinal Chemistry*, vol. 30, No. 8, pp. 1497–1502 (1987).

Jan Otto et al., *Roczniki Chemii*, vol. 47, pp. 967–969 (1973).

Alfons H. M. Raeymaekers et al., "Novel Broad–Spectrum Anthelmintics. Tetramisole[1] and Related Derivatives of 6–Arylimidazo[2,1–b]thiazole", *Journal of Medicinal Chemistry*, vol. 9, No. 4, pp. 545–551 (Jul., 1966).

V. S. Rao et al., "α–(4–Nitro Phenoxy) Chalcones as Synthons for CIS(±)–1,5–Benzothiazepines", *Synthetic Communications*, vol. 30, No. 15, pp. 2763–2768 (2000).

Jörg Schröder et al., "Structure–Based Design and Synthesis of Potent Matrix Metalloproteinase Inhibitors Derived from a 6H–1,3,4–Thiadiazine Scaffold", *Journal of Medicinal Chemistry*, vol. 44, No. 20, pp. 3231–3243 (2001).

David E. Seeger et al., "Synthesis of Two Bis–m–quinomethanes. An Experimental Study of Connectivity Effects on the Equal–Parity Criterion for Low–Spin Ground States in Alternant Non–Kekulé Molecules", *Journal of the American Chemical Society*, vol. 108, No. 6, pp. 1251–1265 (1986).

Wilfrid G. Shaw et al., "The Mesomorphic State: The Mesomorphic 4,4'–Di(n)alkoxybenzalazines", *Journal of the American Chemical Society*, vol. 81, No. 10, pp. 2532–2537 (May, 1959).

Akira Tanaka et al., "Inhibitors of Acyl–CoA:Cholesterol O–Acyltransferase. 2. Identification and Structure–Activity Relationships of a Novel Series of N–Alkyl–N–(heteroaryl-substituted benzyl)–N'–arylureas[1]", *Journal of Medicinal Chemistry*, vol. 41, No. 13, pp. 2390–2410 (1998).

Peter Wan et al, "Disproportionation of 4–Nitroacetophenone to 4–Aminoacetophenone and 4–Nitrobenzoic Acid", *The Journal of Organic Chemsitry*, vol. 54, No. 18, pp. 4473–4474 (1989).

Corrine Y. Watson et al., "Synthesis of 3–Substituted Benzamides and 5–Substituted Isoquinoline–1 (2H)–ones and Preliminary Evaluation as Inhibitors of Poly(ADP–ribose) polymerase (PARP)", *Bioorganic & Medicinal Chemisty*, vol. 6, pp. 721–734 (1998).

James Robert Woodgett, "Use of Peptide Substrates for Affinity Purification of Protein–Serine Kinases", *Analytical Biochemistry*, vol. 180, No. 2, pp. 237–241 (1989).

US 6,747,057 B2

COMPOUNDS AND THEIR THERAPEUTIC USE

TECHNICAL FIELD OF THE INVENTION

The present invention is enclosed within the pharmaceutical research and industry field. In particular, it is centred on the identification of previously described or new chemical compounds useful in the treatment of any pathology related to the phosphorylating activity of the enzyme GSK-3 as, for instance, Alzheimer's Disease, AD.

BACKGROUND OF THE INVENTION

The progressive ageing of the world population brings on the undesired consequence of an increase in the incidence of senile dementia, The most widely spread of this dementia is AD, which affects near 50% of the population aged 85 years or more and, as longevity increases, this rate will also increase unless the strategies to prevent or arrest the neurocdegenerative processes become successful.

There are several biochemical processes affected in AD patients. The treatment of these pathologies would be a correct approach to diminish the damage caused by the disease but, up to now, the only drugs commercialised are some agents that improve cholinergic neurotransmission. Although temporarily, they alleviate the cognoscitive and memory failures associated to AD, At present, most of the research is mainly focused on the search of new agents useful in the treatment of two other pathologies, senile plaques and neurofibrillary tangles, which constitute the major histological lesions observed in AD brains and are also associated with the cholinergic neurotransmission ["Modulation of β-amyloid precursor protein processing and tau phosphorylation by acetylcholine receptors" Hellstr öm-Lindahl, E.; *Eur. J. Pharmacology* 2000, 393, 255–2633].

The object of this invention is precisely related to the discovery of new products which are able to interfere the developing of neurofibrillary tangles. These tangles are formed by paired helical filaments whose main component is an intracellular, polar, quite hydrosoluble, microtubule-associated phosphoprotein protein named tau which appears abnormally phosphorylated. In normal cells, tau is essential for the integrity and stability of the neuronal cytoskeleton but its biological activity appears regulated by the degree of phosphorylation: normal brain tau contains 2–3 moles phosphate/mole protein while AD abnormally hyperphosphorylated tau contains 5–9 moles phosphate/mole protein ["Brain microtubule associated proteins: Modifications and disease" (Kosic, K. and Avila, J. Eds.) Chap. 7: "Tau phosphatases" Iqbal, K. et al. Harwood Academic Publishers, New York, pp. 95–111 (1997)]. Pathological tau presents a diminished capacity to stabilise microtubules, bringing on the corresponding neuronal degeneration, and aggregates into the filaments that form the tangles.

Hyperphosphorylation of tau and progress of AD relation is well demonstrated. Thus, selective inhibitors of the enzymes (kinases) that catalyse the abnormal phosphorylation of tau could become very useful therapeutic agents in the treatment of AD. In fact, the search for these inhibitors is an outstanding field of current pharmaceutical research ["Tau protein as a therapeutic target in Alzheimer's disease and other neurodegenerative diseases" Larner, A. J.; *Expert Opinion on Therapeutic Patents* 1999, 9, 1359–1370].

Neither the whole tau hyperphosphorylation process nor all the kinases involved in it are completely known, but it is clear that GSK-3 is an in vivo kinase in brain and that it plays a central role in the pathological process. The discovery of non-toxic GSK-3 inhibitors would be very important, both from the scientific and industrial points of view, because, until now, the lithium cation is the only agent that have proved to inhibit GSK-3 but in therapeutically unacceptable high concentrations. A comprehensive review on this subject may be found in "Inhibition of tau phosphorylation: a new therapeutic strategy for the treatment of Alzheimer's disease and other neurodegenerative disorders" Castro, A.; Martinez, A.; *Expert Opinion on Therapeutic Patents* 2000, 10, 1519–1527. It has also been observed that insulin inactivates GSK-3 and that non-dependent insulin diabetes mellitus is related to the activation of the enzyme, so, there is the possibility that GSK-3 inhibitors could became new useful agents in the treatment of that kind of diabetes.

Research conducted by the present applicants has recently shown that a new family of aromatic and heteroaromatic ketones exhibit GSK-3 inhibitor activity at a micromolar or lower concentration level, thus leading to the completion of the present invention.

DESCRIPTION OF THE INVENTION

In a first aspect, the present invention provides compounds of general formula I:

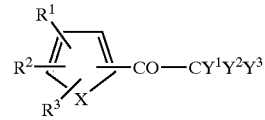

wherein:

X represents —CH=CH—, —CH=CR—, —CR=CR—, —CO—, —O—, —NH—, —NR—, —S—, —SO—, —SO$_2$—, —CH=N—, —CR=N—, —CH=N(O)—, —CR=N(O)— or any other atom or group of atoms capable of forming a 5- or 6-membered heterocyclic ring;

$Y^1$, $Y^2$ and $Y^3$ independently represent hydrogen or halogen;

$R^1$, $R^2$ and $R^3$ are independently represent hydrogen, halogen, hydrocarbyl (—R), hydroxyl (—OH), hydrocarbyloxy (—O—R), mercapto (—SH), hydrocarbylthio (—S—R), hydrocarbylsulfinyl (—SO—R), hydrocarbylsulfonyl (—SO$_2$—R), nitro (—NO$_2$), amino (—NH$_2$), hydrocarbylamino (—NHR), bis(hydrocarbyl)amino (—NR$_2$), hydrocarbylcarbonylamino (—NH—CO—R), cyano (—CN), carbamoyl (—CONH$_2$), hydrocarbylcarbamoyl (—CONHR), bis(hydrocarbyl)carbamoyl (—CONR$_2$), carboxyl (—CO$_2$H), hydrocarbyloxycarbonyl (—CO$_2$R), formyl (—CHO), hydrocarbylcarbonyl (—COR), hydrocarbylcarbonyloxy (—OCOR), optionally substituted heteroaryl or optionally substituted heterocyclic;

the hydrocarbyl group R is a straight or branched chain hydrocarbyl group selected from alkyl, alkenyl, alkynyl, aryl, aralkyl, aralkenyl and aralkynyl, which may optionally be substituted by one or more substituents, selected from those defined above in relation to $R^1$, $R^2$ and $R^3$.

As described below, the compounds of formula (I) are inhibitors of kinases in general and of GSK-3 in particular, and are therefore useful as possible therapeutic agents.

Therefore, in a second aspect, the invention provides the use of a compound of formula (I) as a medicament, in particular in the manufacture of a medicament for the treatment including prophylaxis of diseases mediated by the activation of GSK-3.

In a third aspect, the invention provides a method of treating a mammal, notably a human, affected by a disease mediated by the activation of GSK-3, which comprises administering to the affected individual a therapeutically effective amount of a compound of formula (I), or a pharmaceutical composition thereof.

In further aspects, the present invention provides a pharmaceutical preparation which contain as active ingredient a compound or compounds of the invention, as well as a process for the preparation of such a pharmaceutical.

DETAILED DESCRIPTION OF PREFERRED EMBODIMENTS

In the compounds of formula (I), the hydrocarbyl group R and the hydrocarbyl component of the other groups is a straight or branched chain hydrocarbyl group selected from alkyl, alkenyl, alkynyl, aryl, aralkyl, aralkenyl and aralkynyl. These are defined in more detail below.

In the definitions used in the present application, alkyl groups may be straight or branched chain groups and preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more prefereably 2, 3 or 4 carbon atoms. The terms alkenyl and alkynyl as used herein refer to both cyclic and noncyclic groups, although straight or branched noncyclic groups are generally more preferred.

The aryl groups in the compounds of the present invention preferably have 6 to 10 carbon atoms in a single aromatic carbocyclic ring or in two or more fused rings. Phenyl and naphthyl groups, especially the phenyl group, are preferred.

The aryl groups may optionally be substituted on the aromatic ring by one or more substituents. When more than one substituent is present, the substituents may be the same or different. The number of substituents on the aryl group is restricted only by the number of substitutable positions and by steric constraints. However, we prefer that the aryl groups have from 1 to 5, more preferably 1 to 3, still more preferably 1 or 2, and most preferably only 1 substituent. The substituents may include hydrocarbyl, hydroxyl, hydrocarbyloxy, mercapto, hydrocarbylthio, hydrocarbylsulfinyl, hydrocarbylsulfonyl, nitro, amino, hydrocarbylamino, bis(hydrocarbyl)amino, hydrocarbylcarbonylamino, cyano, carbamoyl, hydrocarbylcarbamoyl, bis(hydrocarbyl)carbamoyl, carboxyl, hydrocarbyloxycarbonyl, formyl, hydrocarbylcarbonyl, hydrocarbylcarbonyloxy, optionally substituted heteroaryl or optionally substituted heterocyclic which are defined in more detail elsewhere in this specification.

Preferred aralkyl groups in the compounds of the present invention comprise an alkyl group having from 1 to 6 carbon atoms which is substituted with an aryl group as defined above to form an aralkyl group having a total of 7 to 16 carbon atoms. The aryl part of the aralkyl group may optionally be substituted on the aromatic ring by one or more substituents, the number and type of which is described above in relation to aryl groups. Examples of preferred aralkyl groups include benzyl, phenethyl, phenylpropyl, 1-naphthylmethyl and naphthylethyl, of which the benzyl group is most preferred.

Preferred aralkenyl and aralkynyl groups in the compounds of the present invention comprise an alkenyl or alkynyl group (preferably having 2 to 6 carbon atoms) which is substituted with an aryl group (as defined above) to form an aralkenyl or aralkynyl group having a total of 8 to 16 carbon atoms. Examples of preferred aralkyl groups include phenylethenyl (styryl) and phenylethynyl.

The hydrocarbyl groups in the compounds of the present invention may be substituted by a number of different groups, including hydrocarbyl, hydroxyl, hydrocarbyloxy, mercapto, hydrocarbylthio, hydrocarbylsulfinyl, hydrocarbylsulfonyl, nitro, amino, hydrocarbylamino, bis(hydrocarbyl)amino, hydrocarbylcarbonylamino, cyano, carbamoyl, hydrocarbylcarbamoyl, bis(hydrocarbyl)carbamoyl, carboxyl, hydrocarbyloxycarbonyl, formyl, hydrocarbylcarbonyl, hydrocarbylcarbonyloxy, optionally substituted heteroaryl or optionally substituted heterocyclic, which are defined in more detail elsewhere in this specification. The number of substituents on the hydrocarbyl group is restricted only by the number of substitutable positions and by steric constraints. However, we prefer that the hydrocarbyl groups have from 1 to 5, more preferably 1 to 3, still more preferably 1 or 2, and most preferably only 1 substituent.

The definitions given above for the various types of hydrocarbyl groups in the compounds of the present invention also apply to the hydrocarbyl part of the other possible groups in these compounds. These are defined in more detail below for the preferred case wherein the hydrocarbyl group is an alkyl group.

Preferred alkoxy groups in the compounds of the present invention include groups having one or more (but preferably only one) oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more (but preferably only one) thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

The halogen atoms in the compounds of the present invention are preferably fluorine, chlorine, bromine or iodine, of which chlorine and bromine are more preferred.

Preferred alkylcarbonyl (alkanoyl) groups in the compounds of the present invention include those groups having one or more carbonyl (CO) groups and from 1 to about 30 carbon atoms, more preferably from 1 to about 12 carbon atoms, and still more preferably 1 to about 6 carbon atoms (including the carbonyl carbon). Alkanoyl groups having 1, 2, 3 or 4 carbon atoms, especially the formyl, acetyl, propionyl, butyryl and isobutyryl groups, are preferred and the acetyl group is especially preferred.

The alkanoyl group may be substituted with one or more (but preferably only one) substituents, which may preferably be selected from halogen, hydroxy, alkoxy and cyano, especially a halogen atom, particularly chlorine or bromine.

Preferred alkylcarbonyloxy (alkanoyloxy) groups in the compounds of the present invention include those groups having one or more carbonyloxy groups and from 1 to about 30 carbon atoms, more preferably from 1 to about 12 carbon atoms, and still more preferably 1 to about 6 carbon atoms (including the carbonyl carbon). When the term "alkanoyloxy" is used, it is to be understood that the group is attached to the rest of the molecule via the oxygen atom. Alkanoyloxy groups having 1, 2, 3 or 4 carbon atoms, especially the formyloxy, acetoxy, propionyloxy, butyryloxy and isobutyryloxy groups, are preferred and the formyloxy and acetyloxy groups especially preferred.

Preferred alkylcarbonylamino (alkanoylamino) groups in the compounds of the present invention include those-groups having an —NH—CO— linkage (the group being attached to the rest of the molecule via the nitrogen atom) and from 1 to about 30 carbon atoms, more preferably from 1 to about 12 carbon atoms, and still more preferably I to about 6 carbon atoms (including the carbonyl carbon). the group is attached to the rest of the molecule via the nitrogen atom. Alkanoylamino groups having 1, 2, 3 or 4 carbon atoms, especially the formylamino, acetylamino, propionylamino, butyrylamino and isobutyrylamino groups, are preferred and the formylamino and acetylamino groups especially preferred.

Preferred N-alkylcarbamoyl groups in the compounds of the present invention comprise a —CO—NH— linkage (the group being attached to the rest of the molecule via the carbonyl carbon) wherein the nitrogen atom is substituted with an alkyl group having from 1 to about 12 carbon atoms, more preferably 1 to about 6 carbon atoms. N-Alkylcarbamoyl groups having 1, 2, 3 or 4 carbon atoms, especially the N-methylcarbamoyl, N-ethylcarbamoyl, N-propylcarbamoyl and N-butylcarbamoyl groups, are particularly preferred.

Preferred dialkylcarbamoyl groups in the compounds of the present invention comprise a —CO—N— linkage (the group being attached to the rest of the molecule via the carbonyl carbon) wherein the nitrogen atom is substituted with two alkyl groups, each having from 1 to about 12 carbon atoms, more preferably 1 to about 6 carbon atoms. The alkyl groups may be the same or different. N,N-Dialkylcarbamoyl groups wherein each alkyl group has 1, 2, 3 or 4 carbon atoms, especially the N,N-dimethylcarbamoyl, N,N-diethylcarbamoyl, N-methyl-N-ethylcarbamoyl, N-ethyl-N-propylcarbamoyl, N,N-dipropylcarbamoyl, N,N-dibutylcarbamoyl and N-methyl-N-butylcarbamoyl groups, are particularly preferred.

Preferred monoalkylamino groups in the compounds of the present invention have one or more (but preferably only one) NH linkages and from 1 to about 12 carbon atoms, more preferably from 1 to about 8 carbon atoms, and still more preferably 1 to about 6 carbon atoms. Alkylamino groups having 1, 2, 3 or 4 carbon atoms, especially the methylamino, ethylamino, propylamino and butylamino groups, are particularly preferred.

Preferred dialkylamino groups in the compounds of the present invention have one or more (but preferably only one) nitrogen atom bonded to two alkyl groups, each of which may from 1 to about 12 carbon atoms, more preferably from 1 to about 8 carbon atoms, and still more preferably 1 to about 6 carbon atoms. The alkyl groups may be the same or different. Dialkylamino groups wherein each alkyl group has 1, 2, 3 or 4 carbon atoms, especially the dimethylamino, diethylamino, N-methylethylamino, N-ethylpropylamino, dipropylamino, dibutylamino and N-methylbutylamino groups, are particularly preferred.

Preferred alkoxycarbonyl groups in the compounds of the present invention include those groups having one or more (but preferably only one) oxycarbonyl groups and from 1 to about 30 carbon atoms, more preferably from 1 to about 12 carbon atoms, and still more preferably 1 to about 6 carbon atoms (including the carbonyl carbon). When the term "alkoxycarbonyl" is used, it is to be understood that the group is attached to the rest of the molecule via the carbonyl carbon. Alkoxycarbonyl groups having 1, 2, 3 or 4 carbon atoms, especially the methoxycarbonyl, ethoxycarbonyl, propoxycarbonyl and butoxycarbonyl are preferred and the methoxycarbonyl and ethoxycarbonyl groups especially preferred.

Heteroaromatic groups in the compounds of the present invention preferably have from 5 to 14 ring atoms in a single aromatic ring or in 2 or more fused rings. At least one of the ring atoms (preferably from 1 to 4 ring atoms, more preferably 1 to 3 ring atoms, even more preferably 1 or 2 ring atoms, and most preferably 1 ring atom) is a heteroatom, which is preferably selected from nitrogen, oxygen and sulfur atoms. The heteroaromatic group may optionally be fused to another heteroaromatic group or to an aryl group, examples of which are defined above. Examples of preferable heteroaromatic groups include pyridyl, furyl, thienyl, imidazolyl, oxazolyl, isoxazolyl, thiazolyl, isothiazolyl, triazolyl, tetrazolyl, pyranyl, pyridyl, pyrimidinyl, pyridazinyl, indolyl, benzimidazolyl, benzofuryl, benzothienyl and benzisoxazolyl.

The heteroaromatic groups in the compounds of the present invention may be substituted by a number of different groups, including hydrocarbyl, hydroxyl, hydrocarbyloxy, mercapto, hydrocarbylthio, hydrocarbylsulfinyl, hydrocarbylsulfonyl, nitro, amino, hydrocarbylamino, bis(hydrocarbyl)amino, hydrocarbylcarbonylamino, cyano, carbamoyl, hydrocarbylcarbamoyl, bis(hydrocarbyl)carbamoyl, carboxyl, hydrocarbyloxycarbonyl, formyl, hydrocarbylcarbonyl, hydrocarbylcarbonyloxy, optionally substituted heteroaryl or optionally substituted heterocyclic, which are defined in more detail elsewhere in this specification. The number of substituents on the heteroaromatic group is restricted only by the number of substitutable positions and by steric constraints. However, we prefer that the heteroaromatic groups have from 1 to 5, more preferably 1 to 3, still more preferably 1 or 2, and most preferably only 1 substituent.

The heterocyclic groups (other than the heteroaromatic groups defined above) in the compounds of the present invention preferably contain from 3 to 14 ring atoms in a single ring or 2 or more fused rings. At least one of the ring atoms (preferably from 1 to 4 ring atoms, more preferably 1 to 3 ring atoms, even more preferably 1 or 2 ring atoms, and most preferably 1 ring atom) is a heteroatom, which is preferably selected from nitrogen, oxygen and sulfur atoms. The heterocyclic group may optionally be fused to a cycloalkyl group, a heterocyclic group, an aryl group or a heteroaromatic groups, examples of which are defined above. Preferred heterocyclic groups include azetidinyl, pyrrolidinyl, tetrahydrofuranyl, tetrahydrothiofuranyl, tetrahydropyranyl, tetrahydrothiopyranyl, piperidinyl, chromanyl and thiochromanyl.

The heterocyclic groups in the compounds of the present invention may be substituted by a number of different groups, including hydrocarbyl, hydroxyl, hydrocarbyloxy, mercapto, hydrocarbylthio, hydrocarbylsulfinyl, hydrocarbylsulfonyl, nitro, amino, hydrocarbylamino, bis(hydrocarbyl)amino, hydrocarbylcarbonylamino, cyano, carbamoyl, hydrocarbylcarbamoyl, bis(hydrocarbyl)carbamoyl, carboxyl, hydrocarbyloxycarbonyl, formyl, hydrocarbylcarbonyl, hydrocarbylcarbonyloxy, optionally substituted heteroaryl or optionally substituted heterocyclic, which are defined in more detail elsewhere in this specification. The number of substituents on the heterocyclic group is restricted only by the number of substitutable positions and by steric constraints. However, we prefer that the heterocyclic groups have from 1 to 5, more preferably 1 to 3, still more preferably 1 or 2, and most preferably only 1 substituent.

Preferably X is selected from —CH=CH—, —CH=CR—, —CR=CR—, —CH=N—, —CR=N—, —O—, —NH—, —NR—, and —S— (the group R representing $C_{1-6}$ alkyl or $C_{6-10}$ aryl).

More preferably, X is selected from —CH=CH—, —CH=CR—, —CR=CR—, —O— and —S— (the group R representing $C_{1-6}$ alkyl).

Most preferably, X is selected from —CH=CH— and —S—.

Preferably, one or two of $Y^1$, $Y^2$ and $Y^3$ are halogen, and the other two or one are hydrogen.

More preferably, one of $Y^1$, $Y^2$ and $Y^3$ is halogen, and the other two are hydrogen.

Most preferably, one of $Y^1$, $Y^2$ and $Y^3$ is chlorine or bromine, and the other two are hydrogen.

Iodo is also a preferred possibility for one of the Y groups, with the other two being hydrogen.

Preferably, $R^1$, $R^2$ and $R^3$ are independently selected from hydrogen, halogen, $C_{1-6}$ alkyl (which may be optionally substituted with one or more substituents selected from halogen, hydroxy, $C_{1-6}$ alkoxy and cyano), $C_{6-10}$ aryl, optionally substituted $C_{7-16}$ aralkyl, hydroxy, $C_{1-6}$ alkoxy, $C_{6-10}$ aryloxy, $C_{7-16}$ aralkyloxy, $C_{1-6}$ alkylthio, $C_{6-10}$ arylthio, $C_{7-16}$ aralkylthio, $C_{1-6}$ alkylsulfinyl, $C_{6-10}$ arylsulfinyl, $C_{7-16}$ aralkylsulfinyl, $C_{1-6}$ alkylsulfonyl, $C_{6-10}$ arylsulfonyl, $C_{7-16}$ aralkylsulfonyl, cyano, carboxyl, $C_{1-6}$ alkyloxycarbonyl, $C_{7-11}$ aryloxycarbonyl, $C_{8-16}$ aralkyloxycarbonyl, heteroaryl and $C_{1-30}$ aliphatic acyl (which may be optionally substituted with one or more substituents selected from halogen, hydroxy and $C_{1-6}$ alkoxy and cyano)).

More preferably, $R^1$, $R^2$ and $R^3$ are independently selected from hydrogen, halogen, $C_{1-6}$ alkyl (which may be optionally substituted with one or more substituents selected from halogen, hydroxy and $C_{1-6}$ alkoxy), $C_{1-6}$ alkoxy, $C_{6-10}$ aryl, heteroaryl, nitro, amino and $C_{1-20}$ aliphatic acyl (which may be optionally substituted with one or more substituents selected from halogen, hydroxy and $C_{1-6}$ alkoxy and cyano).

Still more preferably, $R^1$, $R^2$ and $R^3$ are independently selected from hydrogen, halogen, $C_{1-4}$ alkyl (which may be optionally substituted with one or more halogen atoms), $C_{1-4}$ alkoxy, $C_{6-10}$ aryl, heteroaryl, nitro, amino and $C_{2-6}$ aliphatic acyl (which may be optionally substituted with one or more halogen atoms), provided that at least one of $R^1$, $R^2$ and $R^3$ are other than hydrogen.

Yet more preferably, $R^1$, $R^2$ and $R^3$ are independently selected from hydrogen, chlorine, bromine, methyl, ethyl, methoxy, ethoxy, acetyl, chloroacetyl, phenyl, morpholino, nitro, amino and bromoacetyl, provided that at least one of $R^1$, $R^2$ and $R^3$ is other than hydrogen.

Even more preferably, $R^1$, $R^2$ and $R^3$ are independently selected from hydrogen, chlorine, bromine, methyl, methoxy, phenyl, morpholino, nitro, amino and chloroacetyl, provided that at least one of $R^1$, $R^2$ and $R^3$ is other than hydrogen.

As the person skilled in the art will readily appreciate, the preferred definitions of X, $Y^1$, $Y^2$, $Y^3$, $R^1$, $R^2$, and $R^3$ may be combined in various ways, and the compounds covered by all such combinations and permutations of the above preferred definitions are to be considered as being part of this invention. More especially, we prefer compounds wherein —X— is —S— or —CH=CH—; is bromo-, dibromo-, chloro-, dichloro- or iodo- acetyl; $R^1$ is one of the possibilities listed in Table 1 for $R^1$, $R^2$ or $R^3$; $R^2$ is one of the possibilities listed in Table 1 for $R^1$, $R^2$ or $R^3$; and $R^3$ is one of the possibilities listed in Table 1 for $R^1$, $R^2$ or $R^3$.

Preferred compounds of formula (I) are selected from the following Table 1.

TABLE 1

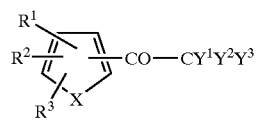

I

| comp. | —X— | $COCY^1Y^2Y^3$ | $R^1$ | $R^2$ | $R^3$ |
|---|---|---|---|---|---|
| 1 | —S— | 3-COCH$_2$Cl | 2-Br | 4-Cl | 5-Cl |
| 2 | —S— | 2-COCH$_2$Cl | 4-Cl | 5-Cl | H |
| 3 | —S— | 2-COCH$_2$Cl | 4-Br | H | H |
| 4 | —S— | 3-COCH$_2$Cl | 4-Cl | H | H |
| 5 | —S— | 3-COCH$_2$Cl | 2-Br | 4-Br | 5-Br |
| 6 | —S— | 3-COCH$_2$Cl | 2-Cl | 5-Cl | H |
| 7 | —S— | 2-COCH$_2$Cl | 5-Cl | H | H |
| 8 | —S— | 2-COCH$_2$Cl | 5-Br | H | H |
| 9 | —S— | 2-COCH$_2$Cl | 4-COCH$_2$Cl | H | H |
| 10 | —S— | 2-COCH$_2$Cl | H | H | H |
| 11 | —S— | 2-COCH$_2$Cl | 4-COCH$_2$Cl | 5-CH$_3$ | H |
| 12 | —S— | 2-COCH$_2$Cl | 5-CH$_3$ | H | H |
| 13 | —S— | 3-COCH$_2$Cl | 2-CH$_3$ | 5-CH$_3$ | H |
| 14 | —S— | 2-COCH$_2$Cl | 4-Br | 5-Br | H |
| 15 | —S— | 2-COCH$_2$Cl | 3-Br | 4-Br | H |
| 16 | —S— | 2-COCH$_2$Cl | 3-CH$_3$ | 4-COCH$_2$Cl | H |
| 17 | —S— | 2-COCH$_2$Cl | 4-CH$_3$ | H | H |
| 18 | —S— | 2-COCH$_2$Cl | 3-CH$_3$ | H | H |
| 19 | —S— | 2-COCH$_2$Cl | 5-COCH$_3$ | H | H |
| 20 | —S— | 2-COCH$_2$Cl | 4-COCH$_3$ | H | H |
| 21 | —S— | 2-COCH$_2$Br | 3-Br | 4-Br | H |
| 22 | —S— | 2-COCH$_2$Br | 4-Br | 5-Br | H |
| 23 | —S— | 2-COCH$_2$Br | 5-Br | H | H |
| 24 | —CH=CH— | COCH$_2$Cl | 4-Cl | H | H |

TABLE 1-continued $$R^2 \underset{R^3}{\overset{R^1}{\diagdown}} X \diagup CO-CY^1Y^2Y^3 \quad I$$

| comp. | —X— | COCY¹Y²Y³ | R¹ | R² | R³ |
|---|---|---|---|---|---|
| 25 | —CH=CH— | COCH₂Cl | H | H | H |
| 26 | —CH=CH— | COCH₂Br | 2-Br | 4-Br | 6-Br |
| 27 | —CH=CH— | COCH₂Br | 3-Br | 4-Br | H |
| 28 | —CH=CH— | COCH₂Br | 4-Br | H | H |
| 29 | —CH=CH— | COCH₂Br | 4-Cl | H | H |
| 30 | —CH=CH— | COCH₂Br | H | H | H |
| 31 | —CH=CH— | COCH₂Br | 4-CH₃ | H | H |
| 32 | —CH=CH— | COCH₂Br | 4-OCH₃ | H | H |
| 33 | —CH=CH— | COCH₂Br | 4-Ph | H | H |
| 34 | —CH=CH— | COCHBrCl | 4-Cl | H | H |
| 35 | —CH=CH— | OCCHBrCl | H | H | H |
| 36 | —CH=CH— | COCHBr₂ | H | H | H |
| 37 | —CH=CH— | COCHBr₂ | 4-Br | H | H |
| 38 | —CH=CH— | COCH₂Br | 4-CN | H | H |
| 39 | —CH=CH— | COCHBr₂ | 4-CN | H | H |
| 40 | —CH=CH— | COCH₂Br | 4-CF₃ | H | H |
| 41 | —CH=CH— | COCHBr₂ | 4-CF₃ | H | H |
| 42 | —CH=CH— | COCH₂Br | 4-Morpholine | H | H |
| 43 | —CH=CH— | COCH₂Br | 3-CN | H | H |
| 44 | —CH=CH— | COCHBr₂ | 3-CN | H | H |
| 45 | —CH=CH— | COCHBr₂ | 4-I | H | H |
| 46 | —CH=CH— | COCH₂Br | 4-NO₂ | H | H |
| 47 | —CH=CH— | COCH₂Br | 3-Br | 4-NH₂ | 5-Br |
| 48 | —CH=CH— | COCH₂I | 4-Br | H | H |

In further aspects, the present invention provides a pharmaceutical preparation, which contains as active ingredient a compound or compounds of the invention, as well as a process for its preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Synthesis of the Compounds of the Invention

Most of the compounds whose biological activity is the object of the present invention can be synthesised following a general procedure previously described [Conde, S.; Corral, C.; Madroñero, R.; Sánchez Alvarez-Insúa, A.; Fernández-Tomé M. P.; del Río. J.; *J. Med. Chem.* 1977, 20, 970–974]. Following this synthetic method, an aromatic or heteroaromatic compound of formula II reacts with a mixture of a substituted acetyl halide of formula III, e. g. chloroacetyl chloride, bromoacetyl bromide, etc, and a Lewis acids, such as TiCl₄, SnCl₄, AlCl₃, etc, in an aprotic anhydrous organic solvent, for example, CS₂, CCl₄, etc. This process is represented in Scheme 1, where Y' represents a halogen atom (F, Cl, Br or I).

Scheme 1

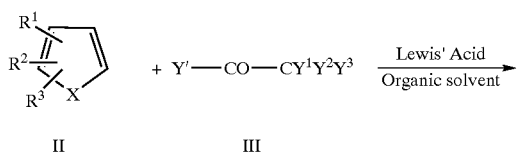

Another group of compounds can be synthesised by the general synthetic procedure of halogenation [described, for example, in: Seeger, D. E.; Lahti, P. M.; Rossi, A. R.; Benson, J. A.; *J. Am. Chem. Soc.* 1986, 108, 1251–1265] represented in Scheme 2. Following this procedure, an aromatic or heteroaromatic ketone IV is treated with the desired halogen in the medium of a polar organic solvent, such as acetic acid, dioxane, etc, to obtain the α-halomethyl ketone V, which falls within the scope of compounds of formula I but has a single halogen atom Y.

Scheme 2

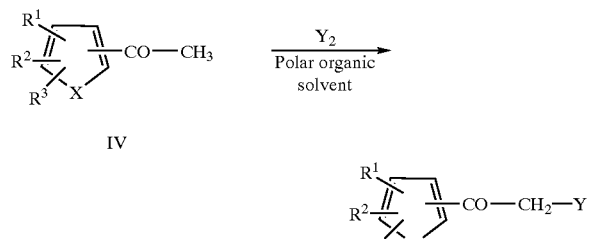

Activity of the Compounds of the Invention

In the following examples, the selective enzyme GSK-3 inhibition by the compounds of the invention is demonstrated. As described above, it has been established that the enzyme GSK-3 plays a crucial role in the ethiopathogenia of AD as responsible of the hyperphosphorylation of the protein tau observed in this pathology. Because of the biological activity of these products as GSK-3 inhibitors, they can be considered as important prototypes or lead compounds of a new family of compounds that can prevent the formation of neurofibrillary tangles and reverse those already formed.

The compounds of the invention are capable of inhibiting the enzyme GSK-3. The compounds of the invention are therefore useful as therapeutical agents in the treatment of neurodegenerative diseases, such as AD or any other associated to the pathology of protein tau, or to the activation of GSK-3, such as non-insulin dependent diabetes mellitus.

In addition, due to their ability to inhibit the cellular cycle, the compounds of the invention are also useful in the treatment of hyperproliferative diseases, for example, displasias and metaplasias of different tissues, psoriasis, arteriosclerosis and cancer. Their application in the treatment of these pathologies forms also part of the present invention.

WO 9640982 provides compositions for therapy of neurodegenerative disease comprising an efficacious amount of a selective $PLA_2$ inhibitor. p-Bromophenacyl bromide is given as an example of such a selective $PLA_2$ inhibitor. The present invention disclaims this use of p-bromophenacyl bromide. In preferred compounds of this invention, a phenacyl bromide is not subsituted with one substituent which is p-bromo, or a p-bromoacetophenone compound does not have one subsituent which is α-bromo, or the compound is not a selective $PLA_2$ inhibitor.

EXAMPLES
Synthesis of Some of the Compounds of the Invention

Examples 1 and 2
1-(2-Bromo-4,5-dichloro-thiophen-3-yl)-2-chloro-ethanone (1) and 2-Chloro-1-(4,5-dichloro-thiophen-2-yl)-ethanone (2) (General Procedure).

Chloroacetyl chloride (4.60 ml, 0.058 mol) was added to a stirred suspension of aluminium trichloride (7.70 g, 0.058 mol) in carbon disulphide (50 ml) placed in a 250 ml round-bottom flask equipped with a reflux condenser, an addition funnel and a magnetic stirring bar. The mixture was stirred at room temperature overnight and then refluxed for 1 h. Afterwards, the reaction was ice-cooled an treated with 1N aqueous HCl (50 ml). The organic layer was separated, washed with water, dried over magnesium sulphate and the solvent evaporated. The residue yielded two compounds by chromatography column (hexane:ethyl acetate 10:1): the compound 1 (9.72 g, 63%) [m.p.:85–86° C. (heptane), $^1$H—NMR (CDCl$_3$): δ=4.68 (s, CH$_2$Cl)] and a second compound (2) identified as 2-chloroacetyl-4,5-dichlorothiophene (2.53 g, 22%), previously described [del Agua et al *J. Heterocyclic Chem.* 1981, 18,1345-1347].

Example 3
1-(4-Bromo-thiophen-2-yl)-2-chloro-ethanone
This compound was previously described by Conde et al [*J. Med. Chem.* 1977, 20, 970–974].

Example 4
2-Chloro-1-(4-chloro-thiophen-3-yl)-ethanone
This compound was previously described by Conde et al [*J. Med. Chem.* 1977, 20, 970–974].

Example 5
2-Chloro-1-(2 4,5-tribromo-thiophen-3-yl) -ethanone.
This compound was previously described by del Agua et al [*J. Heterocyclic Chem.* 1981, 18, 1345–1347].

Example 6
2-Chloro-1-(2,5-dichloro-thiophen-3-yl)-ethanone.
General procedure described for compounds 1 and 2 starting from 2,5-dichlorothiophene and chloroacetyl chloride. Purified by column chromatography column (hexane:ethyl acetate 12:1), yield 91%, m.p.: 43–44° C. (ethanol), $^1$H-NMR (CDCl$_3$): δ7.1 (s, 1H, CH-Aromat), 4.6 (s, 2H, CH$_2$); $^{13}$C-NMR (CDCl$_3$): 186.6 (CO), 136.9 (C—Cl), 136.0 (C—CO), 130.2 (C—Cl), 129.4 (CH—Ar), 50.6 (CH$_2$); M/z (EI): 234, 232, 230, 228 (M$^+$, 1, 6, 16, 16%), 183, 181, 179 (M-CH$_2$Cl, 18, 79, 100%), 155, 153, 151 (M-COCH$_2$Cl, 3, 13, 19%), 118, 116 (M-COCH$_2$Cl$_2$, 5, 13%); HPLC: Delta Pak Column C18, 5 μm, 300 A, (150× 3.9 mm), Purity 99%, r.t.=6.16 min, acetonitrile/H$_2$O (0.05% H$_3$PO$_4$+0.04% Et$_3$N) 50/50.

Example 7
2-Chloro-1-(5-cbloro-thioiphen-2-yl)-ethanone
This compound was previously described by Emerson et al. [*J. Org. Chem.* 1948, 13, 729–730].

Example 8
1-(5-Bromo-thiophen-2-yl)-2-chloro-ethanone.
This compound was previously described by del Agua et al [*J. Heterocyclic Chem.* 1981, 18, 1345–1347].

Examples 9 and 10
2-Chloro-1-[4-(2-chloro-acetyl)-thiophen-2-yl]-ethanone (9) and 2-Chloro-1-thiophen-2-yl-ethanone (10)
General procedure described for compounds 1 and 2 starting from thiophene and chloroacetyl chloride. Two products were isolated by column chromatography column (hexane:ethyl acetate 4:1). Compound 9: yield 68%, m.p.: 154–155° C. (water/methanol), $^1$H-NMR (CDCl$_3$): δ8.4 (s, 1H, H$_5$), 8.2 (s, 1H, H$_3$), 4.6 (s, 2H, CH$_2$), 4.5 (s, 2H, CH$_2$); $^{13}$C-NMR (CDCl$_3$): δ189.0 (CO), 188.2 (CO), 145.9 (C—CO), 144.3 (CH), 143.3 (C—CO), 135.9(CH), 49.7 (CH$_2$), 49.1 (CH$_2$); M/z (EI): 240, 238, 236 (M$^+$, 1, 2, 8%), 189, 187 (M-CH$_2$Cl, 39, 100%); HPLC: Delta Pak Column C18, 5 μm, 300 A, (150×3.9 mm), Purity 96%, r.t.=3.21 min, acetonitrile/H$_2$O (0.05% H$_3$PO$_4$+0.04% Et$_3$N)]50/50. Compound 10 (13%) was previously described by Nakayama, J. et al [*Heterocycles.* 1987, 26, 10, 2599–2602].

Examples 11 and 12
2-Chloro-1-[4-(2-chloro-acetyl)-5-methyl-thiophen-2-yl]-ethanone (11) and 2-Chloro-1-(5-methyl-thiophen-2-yl)-ethanone (12)
General procedure described for compounds 1 and 2 starting from 2-methylthiophene and chloroacetyl chloride. Two products were isolated by column chromatography column (hexane:ethyl acetate 6:1). Compound 11: yield 73%, mrp.: 110–111° C. (hexane), $^1$H—NMR (CDCl$_3$): δ8.0 (s, 1H, Ar), 4.54 (s, 2H, CH$_2$), 4.52 (s, 2H, CH$_2$), 2.8 (s, 3H, CH$_3$); $^{13}$C-NMR (CDCl$_3$): δ190.3 (CO), 187.7 (CO), 164.6 (C—CH$_3$), 140.3 (C—CO), 137.4 (C—CO), 137.1 (CH), 51.2 (CH$_2$), 48.9 (CH$_2$), 21.1 (CH$_3$); M/z (EI): 254, 252, 250 (M$^+$, 2, 11, 15%), 203, 201 (M-CH$_2$Cl, 52, 100%); HPLC: Delta Pak Column C18, 5 μm, 300 A, (150×3.9 mnm), Purity 94%, r.t.=3.89 min, acetonitrile/H$_2$O (0.05% H$_3$PO$_4$+0.04% Et$_3$N) 50/50. Compound 12 (8%), was previously described by Belenkii et al [*J. Org. Chem.* 1970, 6, 2531–2534].

Example 13
2-Chloro-1-(2,5 dimethyl-thiophen-3-yl) -ethanone.
This compound was previously described by Belenkii et al [*J. Org. Chem.* 1970, 6, 2531–2534].

Example 14
2-Chloro-1-(4,5-dibromo-thiophen-2-yl)-ethanone.
This compound was previously described by del Agua et al [*J. Heterocyclic Chem.* 1981, 18, 1345–1347].

Example 15
2-Chloro-1-(3,4-dibromo- thiophen-2-yl)-ethanone.
General procedure described for compounds 1 and 2 starting from 3,4-dibromothiophene and chloroacetyl chloride. The product was isolated by column chromatography column (hexane:ethyl acetate 8:1). Yield 97%, m.p.: 86–8° C., $^1$H-NMR (CDCl$_3$): δ7.7 (s, 1H, Ar), 4.8 (s, 2H, CH$_2$); $^{13}$C-NMR (CDCl$_3$): δ185.4 (CO), 140.0 (C—CO), 133.7 (CH), 120.8 (C—Br), 119.6 (C—Br), 50.1 (CH$_2$); M/z (EI): 322, 320, 318, 316 (M$^+$, 3, 11, 15, 7%), 271, 269, 267 (M-CH$_2$Cl, 56, 100, 56%); HPLC: Delta Pak Column C18, 5 μm, 300 A, (150×3.9 mm), Purity 94%, r.t.=6.06 min, acetonitrile/H$_2$O (0.05% H$_3$PO$_4$+0.04% Et$_3$N) 50/50.

Examples 16, 17 and 18

2-Chloro-1-[5-(2-chloro-acetyl)-4-methyl-thiophen-3-yl]-ethanone (16), 2-Chloro-1-(4-methyl-thiophen-2-yl)-ethanone (17) and 2-chloro-1-(3-methyl-thiophen-2-yl)-ethanone (18)

General procedure described for compounds 1 and 2 starting from 3-methylthiophene and chloroacetyl chloride. Three products were isolated by column chromatography column (hexane:ethyl acetate 3:1). Compound 16: yield 69%, m.p.: 155–156° C., $^1$H-NMR (CDCl$_3$): δ8.2 (s, 1H, Ar), 4.54 (s, 2H, CH$_2$), 4.52 (s, 2H, CH$_2$), 2.8 (s , 3H, CH$_3$); $^{13}$C-NMR (CDCl$_3$): δ187.2 (CO), 185.1 (CO), 148.2 (C—CO), 139.1 (C—CO), 137.9 (CH), 48.1 (CH$_2$), 47.3 (CH$_2$), 16.0 (CH$_3$); M/z (EI): 254, 252, 250 (M$^+$, 1, 6, 9%), 203, 201 (M-CH$_2$Cl, 47, 100%); HPLC: Column μ Bondapack C18, 5 μm, 300 A, (300×3.9 mm), Purity 99%, r.t.=4.73 min, acetonitrile/H$_2$O (0.05% H$_3$PO$_4$+0.04% Et$_3$N) 50/50. Compound 17: yield 8%, m.p.; 76–77° C., $^1$H-NMR (CDCl$_3$): δ7.6 (s, 1H, Ar), 7.1 (s, 1H, Ar), 4.55 (s, 2H, CH$_2$), 2.3 (s , 3H, CH$_3$); $^{13}$C-NMR (CDCl$_3$): δ188.1 (CO), 144.2 (C—CO), 143.2 (C—CH$_3$), 138.9 (CH), 134.9 (CH), 49.4 (CH$_2$), 19.5 (CH$_3$); M/z (EI): 176, 174 (M$^+$, 9, 23%), 125 (M-CH$_2$Cl, 100%); HPLC: Column μ Bondapack C18, 5 μm, 300 A, (300×3.9 mm), Purity 98%, r.t.=4.56 min, Conditions Acetonitrile/H$_2$O [(0.05% H$_3$PO$_4$+0.04% Et$_3$N)] 50/50. Compound 18 yield 5%, yellow oil, $^1$H-NMR (CDCl$_3$): δ7.44 (d, J=4.9 Hz, 1H, Ar), 7.0 (d, J=4.9 Hz, 1H, Ar), 4.55 (s, 2H, CH$_2$), 2.3 (s ,3H, CH$_3$); $^{13}$C-NMR (CDCl$_3$): δ188.2 (CO), 151.3 (C—CH$_3$), 136.8 (CH), 136.2 (C—CO), 135.0 (CH), 51.5 (CH$_2$), 20.9 (CH$_3$); M/z (EI): 176, 174 (M$^+$, 6, 16%), 125 (M-CH$_2$Cl, 100%); HPLC: Column μ Bondapack C18, 5 μm, 300 A, (300×3.9 mm), Purity 99%, r.t.=3.65 min, acetonitrile/H$_2$O (0.05% H$_3$PO$_4$+0.04% Et$_3$N) 50/50.

Example 19

1-(5-Acetyl-thiophen-2-yl)-2-chloro-ethanone.

General procedure described for compounds 1 and 2 starting from 2-acetylthiophene and chloroacetyl chloride. Purified by column chromatography column (hexane:ethyl acetate 3:1), yield 25%, m.p.: 94–95° C., $^1$H-NMR (CDCl$_3$): δ8.3 (d, J=4.2 Hz, 1H, Ar), 8.1 (d, J=4.2 Hz, 1H, Ar), 4.55 (s, 2H, CH$_2$), 2.6 (s, 3H, CH$_3$); $^{13}$C-NMR (CDCl$_3$). δ193.0 (CO), 187.8 (CO), 148.3 (C—CO), 142.0 (CH), 141.7 (C—CO), 133.7 (CH), 48.3 (CH$_2$), 29.2 (CH$_3$); M/z (EI): 204, 202 (M $^+$, 4, 10%), 153 (M-CH$_2$Cl, 100%); HPLC: Column μ Bondapack C18, 5 μm, 300 A, (300×3.9 mm), Purity 98%, r.t.=3.50 min, acetonitrile/H$_2$O (0.05% H$_3$PO$_4$+ 0.04% Et$_3$N) 50/50.

Example 20

1-(4-Acetyl-thiophen-2-yl)-2-chloro-ethanone.

General procedure described for compounds 1 and 2 starting from 3-acetylthiophene and chloroacetyl chloride. Purified by column chromatography column (hexane:ethyl acetate 2:1), yield 41% m.p.: 118–119° C., $^1$H-NMR (CDCl$_3$): δ8.3 (s, 1H, Ar), 8.1 (s, 1H, Ar), 4.60 (s, 2H, CH$_2$), 2.56 (s, 3H, CH$_3$); $^{13}$C-NMR (CDCl$_3$): δ191.6 (CO), 184.5 (CO), 143.3 (C—CO), 141.7 (C—CO), 139.7 (CH), 132.0 (CH), 45.4 (CH$_2$), 27.4 (CH$_3$); M/z (EI): 204, 202 (M$^+$, 6, 17%), 153 (M-CH$_2$Cl, 100%); HPLC: Delta Pak Column C18, 5 μm, 300 A, (150×3.9 mm), Purity 94%, r.t.=2.70 min, acetonitrile/H$_2$O (0.05% H$_3$PO$_4$+0.04% Et$_3$N) 50/50.

Example 21

2-Bromo-1-(3,4-dibromo-thiophen-2-yl)-ethanone.

This compound was previously described by Bagli et al [*Can. J. Chem.* 1975, 53, 2598].

Example 22

2-Bromo-1-(4,5-dibromo-thiophen-2-yl)-ethanone.

This compound was previously described by Bagli et al [*Can. J. Chem.* 1975) 53, 2598].

Example 23

2-Bromo-1-(5-bromo-thiophen-2-yl)-ethanone.

This compound was previously described by Raeymaekers et al. [*J. Med. Chem.* 1966, 9, 545–551].

Example 24

2-Chloro-1-(4-chloro-phenyl)-ethanone.

This compound was previously described by Rao et al. [*Synth. Commun.* 2000, 30, 15, 2763–2768].

Example 25

2-Chloro-1-phenyl-ethanone.

This compound was previously described by Rao et al. [*Synth. Commun.* 2000, 30, 15, 2763–2768].

Example 26

2-Bromo-1-(2,4,6-tribromo-phenyl)-ethanone.

General procedure described for compounds 1 and 2 starting from 1,3,5-tribromobenzene and bromoacetyl bromide. Purified by column chromatography column (hexane:ethyl acetate 6:1), yield 45% m.p.: 86–87° C., $^1$H-NMR (CDCl$_3$): δ7.7 (s, 2H, Ar), 4.44 (s, 2H, CH$_2$); $^{13}$C-NMR (CDCl$_3$): δ193.4 (CO), 139.4 (C—CO), 134.5 (CH), 124.7 (C—Br), 119.4 (C—Br), 34.6 (CH$_2$); M/z (EI): 440, 438, 436, 434, 432 (M$^+$, 1, 3, 5, 3, 1%), 345, 343, 341, 339 (M-CH$_2$Br, 35, 96, 100, 41%); HPLC: Column μ Bondapack C18, 5 μm, 300 A, (300×3.9 mm), Purity 98%, r.t.=3.40 min, acetonitrile/H$_2$O (0.05% H$_3$PO$_4$+0.04% Et$_3$N) 50/50.

Example 27

2-Bromo-1-(3,4-dibromo-phenyl)-ethanone.

General procedure described for compounds 1 and 2 starting from 1,2-dibromobenzene and bromoacetyl bromide. Purified by column chromatography column (hexane:ethyl acetate 6:1), yield 13% m.p. 60–61° C., $^1$H-NMR (CDCl$_3$): δ8.2 (s, 1H, Ar), 7.8 (d, 2H, Ar), 4.4 (s, 2H, CH$_2$); $^{13}$C-NMR (CDCl$_3$): δ189.7 (CO), 134.6 (CH), 134.4 (CH), 134.3 (C—CO), 132.0 (C—Br), 128.8(CH), 126.2 (C—Br), 30.4 (CH$_2$); M/z (EI): 360, 358, 356, 354 (M$^+$, 5, 14, 14, 5%), 265, 263, 261 (M-CH$_2$Br, 62, 100, 65%); HPLC: Column μ Bondapack C18, 5 μm, 300 A, (300×3.9 mm), Purity 98%, r.t.=8.73 min, acetonitrile/H$_2$O (0.05% H$_3$PO$_4$+0.04% Et$_3$N) 50/50.

Example 28

2-Bromo-1-(4-bromo-phenyl)-ethanone.

This compound was previously described by Huff et al [*Heterocycles.* 1997, 45, 7, 1363–1384].

Example 29
2-Bromo-1-(4-chloro-phenyl)-ethanone.

This compound was previously described by Collet et al [*Bull. Soc. Chim. Fr.*1899, 21, 67].

Example 30
2-Bromo-1-phenyl-ethanone.

This compound was previously described by Collet et al [*Bull. Soc. Chim. Fr.*1897, 76].

Example 31
2-Bromo-1-p-tolyl-ethanone.

This compound was previously described by Huff et al [*Heterocycles.* 1997, 45, 7, 1363–1384].

Example 32
2-Bromo-1-(4-methoxy-phenyl)-ethanone.

This compound was previously described by Kunckell et al [*Chem. Ber.*1898, 31, 173]

Example 33
1-Biphenyl-4-yl-2-bromo-ethanone.

This compound was previously described by Barfknecht et al [*J. Med. Chem,* 1975, 18, 1161–1164].

Example 34
2-Bromo-2-chloro-1-(4-chloro-phenyl)-ethanone.

This compound was previously described by Otto et al [*Rocz. Chem.*1973, 47, 967–969].

Example 35
2-Bromo-2-chloro-1-phenyl-ethanone.

This compound was previously described by Barluenga et al. [*J. Chem. Soc. Perkin Trans.* 1.1991, 2, 297–300].

Example 36
2,2-Dibromo-1-phenyl-ethanone.

This compound was previously described by Magen et al. [*Tetrahedron. Lett,* 1984, 25, 31, 3369–3372].

Example 37
2,2-Dibromo-1-(4-bromo-phenyl)-ethanone.

This compound was previously described by Klingenberg et al. [*Org. Synth. Coll. Vol, IV* 1963, 110].

Example 38
4-(2-Bromoacetyl)-benzonitrile.

This compound was previously described by Ogata, M et al. [*J. Med. Chem,* 1987, 30, 8, 1497–1502].

Example 39
4-(2,2-Dibromo-acetyl)-benzonitrile.

This compound was previously described by Izawa et al. [*Bull. Chem. Soc. Jpn,* 1983, 56, 5, 1490–1496].

Example 40
2-Bromo-1-(4-trifluoromethyl-phenyl)-ethanone.

This compound was previously described by Schroeder et al. [*J. Med. Chem,* 2001, 44, 20, 3231–3243].

Example 41

2,2-Dibromo-1-(4-trifluoromethyl-phenyl)-ethanone.

This compound was synthesised by the general procedure represented in Scheme 2, a stirred solution of 1-(4-trifluoromethyl-phenyl)-ethanone (1 g, 5.3 mmol) ) and acetic acid (50 ml) was refluxed 1 h, then bromine (0.35 ml, 6.9 mmol) was added dropwise and the mixture refluxed 3 h. After cooling at room temperature, water (50 ml) was added and the mixture extracted with $CH_2Cl_2$ (50 ml), the organic layer was washed with water (50 ml), a solution of $NaHCO_3$ saturated (50 ml) and finally with NaCl solution (50 ml), the organic layer was dried over sodium sulphate and the solvent evaporated under reduced pressure. The resulting residue was purified by column chromatography, using a mixture of ethyl acetate:hexane (1:8) as eluent giving two compounds, the titled compound 41 as a yellow solid (45%) m.p.: 40–41° C., $^1$H-NMR ($CDCl_3$): δ8.2 (d, J=8.3 Hz, 2H, Ar), 7.8 (d, J=8.3 Hz, 2H, Ar), 6.6 (s, 1H, CH); $^{13}$C-NMR ($CDCl_3$): δ184.1 (CO), 134.7 (q, J=272.9 Hz, C—$CF_3$), 132.7 (C—CO), 129.2 (CH), 124.8 (CH), 119.5 (q, J=33.09, $CF_3$), 38.2 (CH); M/z (EI): 348, 346, 344 (M$^+$, 1, 6, 1%), 173 (M-CHBr$_2$, 100%); HPLC: Column μ Bondapack C18, 5 μm, 300 A, (300×3.9 mm), Purity 97%, r.t.=9.96 min, acetonitrile/$H_2O$ (0.05% $H_3PO_4$+0.04% $Et_3N$) 50/50. The second compound was identified as 2-bromo-1-(4-trifluoromethyl-phenyl)-ethanone (0,6%), described as the example 40.

Example 42
2-Bromo-1-(4-morpholin-4-yl-phenyl)-ethanone.

This compound was previously described by Diwu et al. [*Tetrahedron. Lett,* 1998, 39, 28, 4987–4990].

Example 43
3-(2-Bromo-acetyl)-benzonitrile.

This compound was previously described by Tanaka et al. [*J. Med. Chem,* 1998, 41, 13, 2390–2410].

Example 44
3-(2,2-Dibromo-acetyl)-benzonitrile.

This compound was previously described by Watson et al. [*Bioorg. Med. Chem,* 1998, 6, 6, 721–734].

Example 45
2,2 -Dibromo-1-(4-iodo-phenyl)-ethanone.

Procedure described in example 41 starting from 4-iodoacetophenone. The resulting residue was purified by column chromatography, using a mixture of hexane:ethyl acetate (6:1) as eluent. Yield 48%, colorless solid m.p.: 77–78° C., $^1$H-NMR ($CDCl_3$): δ7.8 (d, J=4.2 Hz, 2H, Ar), 7.7 (d, J=4.2 Hz, 2H, Ar), 6.3 (s, 1H, CH); $^{13}$C-NMR ($CDCl_3$): δ185.8 (CO), 138.6 (CH), 131.3 (CH), 130.4 (C—CO), 103.4 (C—I), 39.6 (CH); M/z (EI): 406, 404, 402 (M$^+$, 9, 17, 9%), 231, (M-CHBr$_2$, 100%); HPLC: Column Symmetry C18, 5 μm, 300 A, (150×3.9 mm), Purity 94%, r.t.=4.51 min, Conditions Acetonitrile/$H_2O$ (0.05% $H_3PO_4$+ 0.04% $Et_3N$) 50/50.

Example 46
2-Bromo-1-(4-nitro-phenyl)-ethanone.

This compound was previously described by Wan et al [*J. Org. Chem,* 1989, 54, 18, 4473–4474].

Example 47

1-(4-Amino-3,5-dibromo-phenyl)-2-bromo-ethanone.

Procedure described in example 41 starting from p-aminoacetophenone and using chloroform as solvent. The final residue was purified by column chromatography, using a mixture of hexane:ethyl acetate (2:1) as eluent. Yield 58% m.p.: 146–147° C. (ethanol), $^1$H-NMR ($CDCl_3$): δ8.0 (s, 2H, Ar), 5.1 (s, 2H, $NH_2$), 4.2 (s, 2H, $CH_2$); $^{13}$C-NMR ($CDCl_3$): δ187.5 (CO), 147.3 (C—$NH_2$), 132.7 (CH), 123.3 (C—CO), 106.2 (C—Br), 38.3 ($CH_2$); M/z (EI): 375, 373, 371, 369

($M^+$, 10, 31, 31, 10%), 280, 278, 276 (M-CH$_2$Br, 64, 100, 67%); HPLC: Column Symmetry C18, 5 μm, 300 A, (150× 3.9 mm), Purity 96%, r.t.=9.98 min, acetonitrile/H$_2$O (0.05% H$_3$PO$_4$+0.04% Et$_3$N) 50/50.

Example 48
2-Iodo-1-(4-bromo-phenyl)-ethanone.

This compound was previously described by Shaw et al. [*J. Amer. Chem. Soc*, 1959, 81, 2532–2537].

EXAMPLES

Biological Activity as Enzymatic Inhibitors of the Compounds of the Invention

1. Inhibition of GSK-3.

The GSK-3 inhibitory activity of the compound mentioned in this invention was measured by using a previously described method [Woodget, J. R.; *Anal. Biochem.* 1989, 180, 237–241]. This method consists of the incubation of commercially available GSK-3 with a phosphate source and a GSK-3 substrate in the presence and absence of the corresponding compound to be tested, and the measurement of the GSK-3 activity in both mixtures.

In particular, the enzyme was incubated at 37° C. for a 20 minutes period in buffer [tris pH=7.5 (50 mM), EDTA (1 mM), EGTA (1 mM), DTT (1 mM) and MgCl$_2$ (10 mM)] supplemented by the synthetic peptide GS 1 (15 μM final concentration) as substrate, ATP (15 μM), [γ-$^{32}$P]ATP (0.2 μC$_i$) and different concentrations of the product to be tested. After that, aliquots of the reaction mixtures are added on phosphocellulose p81 papers. These papers are washed three times with phosphoric acid 1% and the radioactivity incorporated to the GS 1 peptide is measured in a liquid scintillation counter.

Table 2 shows the data of GSK-3 inhibition, which is the object of this invention, of some representative compounds. The examples presented are explanatory and must be regarded as non-limitative in respect of the scope of protection. The numbers given with the different substituents represents the position of the substituent in the corresponding ring, in accordance with the IUPAC nomenclature rules. The GSK-3 inhibition data given as the inhibitory concentration 50, IC$_{50}$, defined as the concentration of the compound that inhibits the enzyme at 50%.

TABLE 2

| comp. | —X— | COCY$^1$Y$^2$Y$^3$ | R$^1$ | R$^2$ | R$^3$ | IC$_{50}$ (μM) |
|---|---|---|---|---|---|---|
| 1 | —S— | 3-COCH$_2$Cl | 2-Br | 4-Cl | 5-Cl | 2 |
| 2 | —S— | 2-COCH$_2$Cl | 4-Cl | 5-Cl | H | 2.5 |
| 3 | —S— | 2-COCH$_2$Cl | 4-Br | H | H | 3 |
| 4 | —S— | 3-COCH$_2$Cl | 4-Cl | H | H | 25 |
| 5 | —S— | 3-COCH$_2$Cl | 2-Br | 4-Br | 5-Br | 1 |
| 6 | —S— | 3-COCH$_2$Cl | 2-Cl | 5-Cl | H | 5 |
| 7 | —S— | 2-COCH$_2$Cl | 5-Cl | H | H | 10 |
| 8 | —S— | 2-COCH$_2$Cl | 5-Br | H | H | 10 |
| 9 | —S— | 2-COCH$_2$Cl | 4-COCH$_2$Cl | H | H | 1.5 |
| 10 | —S— | 2-COCH$_2$Cl | H | H | H | 50 |
| 11 | —S— | 2-COCH$_2$Cl | 4-COCH$_2$Cl | 5-CH$_3$ | H | 5 |
| 12 | —S— | 2-COCH$_2$Cl | 5-CH$_3$ | H | H | 100 |
| 13 | —S— | 3-COCH$_2$Cl | 2-CH$_3$ | 5-CH$_3$ | H | 100 |
| 14 | —S— | 2-COCH$_2$Cl | 4-Br | 5-Br | H | 1 |
| 15 | —S— | 2-COCH$_2$Cl | 3-Br | 4-Br | H | 0.5 |
| 16 | —S— | 2-COCH$_2$Cl | 3-CH$_3$ | 4-COCH$_2$Cl | H | 2.5 |
| 17 | —S— | 2-COCH$_2$Cl | 4-CH$_3$ | H | H | 100 |
| 18 | —S— | 2-COCH$_2$Cl | 3-CH$_3$ | H | H | 75 |
| 19 | —S— | 2-COCH$_2$Cl | 5-COCH$_3$ | H | H | 50 |
| 20 | —S— | 2-COCH$_2$Cl | 4-COCH$_3$ | H | H | 8 |
| 21 | —S— | 2-COCH$_2$Br | 3-Br | 4-Br | H | 1 |
| 22 | —S— | 2-COCH$_2$Br | 4-Br | 5-Br | H | 1 |
| 23 | —S— | 2-COCH$_2$Br | 5-Br | H | H | 1 |
| 24 | —CH=CH— | COCH$_2$Cl | 4-Cl | H | H | 2.5 |
| 25 | —CH=CH— | COCH$_2$Cl | H | H | H | 50 |
| 26 | —CH=CH— | COCH$_2$Br | 2-Br | 4-Br | 6-Br | 25 |
| 27 | —CH=CH— | COCH$_2$Br | 3-Br | 4-Br | H | 0.75 |
| 28 | —CH=CH— | COCH$_2$Br | 4-Br | H | H | 0.5 |
| 29 | —CH=CH— | COCH$_2$Br | 4-Cl | H | H | 1 |
| 30 | —CH=CH— | COCH$_2$Br | H | H | H | 5 |
| 31 | —CH=CH— | COCH$_2$Br | 4-CH$_3$ | H | H | 2.5 |
| 32 | —CH=CH— | COCH$_2$Br | 4-OCH$_3$ | H | H | 1 |
| 33 | —CH=CH— | COCH$_2$Br | 4-Ph | H | H | 2.5 |
| 34 | —CH=CH— | COCHBrCl | 4-Cl | H | H | 7.5 |
| 35 | —CH=CH— | COCHBrCl | H | H | H | 5 |
| 36 | —CH=CH— | COCHBr$_2$ | H | H | H | 2.5 |
| 37 | —CH=CH— | COCHBr$_2$ | 4-Br | H | H | 0.75 |
| 38 | —CH=CH— | COCH$_2$Br | 4-CN | H | H | 1.5 |
| 39 | —CH=CH— | COCHBr$_2$ | 4-CN | H | H | 1.5 |
| 40 | —CH=CH— | COCH$_2$Br | 4-CF$_3$ | H | H | 5 |
| 41 | —CH=CH— | COCHBr$_2$ | 4-CF$_3$ | H | H | 5 |
| 42 | —CH=CH— | COCH$_2$Br | 4-Morpholine | H | H | 6 |
| 43 | —CH=CH— | COCH$_2$Br | 3-CN | H | H | 1 |
| 44 | —CH=CH— | COCHBr$_2$ | 3-CN | H | H | 1 |
| 45 | —CH=CH— | COCHBr$_2$ | 4-I | H | H | 2 |
| 46 | —CH=CH— | COCH$_2$Br | 4-NO$_2$ | H | H | 2 |
| 47 | —CH=CH— | COCH$_2$Br | 3-Br | 4-NH$_2$ | 5-Br | 3 |
| 48 | —CH=CH— | COCH$_2$I | 4-Br | H | H | 3 |

2. In vitro Effects of Some Compounds on Tau Phosphorilation in Cultured Neurones.

Primary cultured cerebellar neurones were obtained from 7-days old rat following the procedure described by Levy et al. [*Brain Res* 1984, 290, 77–86]. Experiments were performed at 40–48 hours in vitro. Each compound was added at increasing concentrations following the range described in Table 3.

Cells were harvested after 16 hours of treatment and homogenised in a buffer containing 20 mM Hepes, pH 7.4; 100 mM NaCl; 100 mMNa F; 1 mM sodium ortho-vanadate; 5 mM EDTA; and protease inhibitors Complete™.

Tau-1 antibody was used to monitor the tau phosphorylation changes because it is sensitive to dephosphorylation. In addition antibody 7.51 was used to detect the total amount of tau in our cultured neurones. The detection was realised in Western blots and the data quantified using an imaging densitometer (GS-710 model, BioRad)

Table 3 shows the data of Tau phosphorylation inhibition in neurones measured by Tau-1 immunoreactivity obtained from two representative compounds of this invention. The examples presented are for the purposes of explanation and are non-limitative of the scope of protection. The numbers given with the different substituents represents the position of the substituent in the corresponding ring, in accordance with the IUPAC nomenclature rules.

The $IC_{50}$, in this case, is defined as the concentration of the compound that produce the inhibition of tau 1-immunoreactivity in this specific epitope at a 50%

TABLE 3

| —X— | CO—CY$^1$Y$^2$Y$^3$ | R$^1$ | R$^2$ | R$^3$ | $IC_{50}(\mu M)$ |
|---|---|---|---|---|---|
| —S— | 3-CO—CH$_2$Cl | 2-Br | 4-Br | 5-Br | 30 |
| —S— | 3-CO—CH$_2$Cl | 2-Br | 4-Cl | 5-Cl | 30 |

What is claimed is:

1. A method of treatment of a disease mediated by the activation of GSK-3 in a subject in need thereof the method comprising administering to the subject an effective amount of a compound of formula (I):

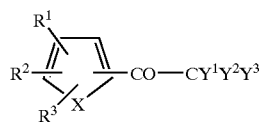

wherein:
X represents —S—, —SO—, or —SO$_2$;
Y$^1$, Y$^2$ and Y$^3$ independently represent hydrogen or halogen;
R$^1$, R$^2$ and R$^3$ are independently represent hydrogen, halogen, hydrocarbyl (—R), hydroxyl (—OH), hydrocarbyloxy (—0—R), mercapto (—SH), hydrocarbylthio (—S—R), hydrocarbylsulfinyl (—SO—R), hydrocarbylsulfonyl (—SO$_2$—R), nitro (—NO$_2$), amino (—NH$_2$), hydrocarbylaniino (—NHR), bis(hydrocarbyl)amino (—NR$_2$), hydrocarbylcarbonylamino (—NH—CO—R), cyano (—CN), carbarnoyl (—CONH$_2$) hydrocarbylcarbarnoyl (—CONHR), bis(hydrocarbyl)carbarnoyl (—CONH$_2$), carboxyl (—C0$_2$H), hydrocarbyloxycarbonyl (—CO$_2$R), formyl (—CHO), hydrocarbylcarbonyl (—COR), hydrocarbylcarbonyloxy (—OCOR), optionally substituted heteroarvi or optionally substituted heterocyclic; and the hydrocarbyl group R is a straight or branched chain hvdrocarbvl aroup selected from alkyl, alkenyl, alkynyl, aryl, aralkyl, aralkenyl and aralkynyl, which may optionally be substituted by one or more substituents, selected from those defined above in relation to R$^1$, R$^2$ and R$^3$, or a pharmaceutical composition thereof.

2. The method of claim 1, wherein X is —S—.

3. The method of claim 1, wherein one or two of Y$^1$, Y$^2$ and Y$^3$ are halogen, and the other two or one are hydrogen.

4. The method of claim 1, wherein one of Y$^1$, Y$^2$ and Y$^3$ is halogen, and the other two are hydrogen.

5. The method of claim 1, wherein one of Y$^1$, Y$^2$ and Y$^3$ is chlorine, bromine or iodine, and the other two are hydrogen.

6. The method of claim 1, wherein R$^1$, R$^2$ and R$^3$ are independently selected from hydrogen; halogen; $C_{1-6}$ alkyl, which is optionally substituted with one or more substituents selected from halogen, hydroxy, $C_{1-6}$ alkoxy and cyano; $C_{6-10}$ aryl; optionally substituted $C^{7-16}$ aralkyl; hydroxy; $C_{1-6}$ alkoxy; $C_{6-10}$ aryloxy; $C_{7-16}$ aralkyloxy; $C_{1-6}$ alkylthio; $C_{6-10}$ arylthio; $C_{7-16}$ aralkylthio; $C_{1-6}$ alkylsulfinyl; $C_{6-10}$ arylsulfinyl; $C_{7-16}$ aralkylsulfinyl; $C_{1-6}$ alkylsulfonyl; $C_{6-10}$ arylsulfonyl; $C_{7-16}$ aralkylsulfonyl; cyano; carboxyl; $C_{1-6}$ alkyloxycarbonyl; $C_{7-11}$ aryloxycarbonyl; $C_{8-16}$ aralkyloxycarbonyl; heteroaryl; or $C_{1-30}$ aliphatic acyl, which is optionally substituted with a halogen atom.

7. The method of claim 1, wherein R$^1$, R$^2$ and R$^3$ are independently selected from hydrogen; halogen; $C_{1-6}$ alkyl, which is optionally substituted with one or more substituents selected from halogen, hydroxy and $C_{1-6}$ alkoxy; $C_{1-6}$ ; alkoxy $C_{6-10}$ aryl; heteroaryl; intro; amino; and $C_{1-20}$ aliphatic acyl, which is optionally substituted with one or more substituents selected from halogen, hydroxy and $C_{1-6}$ alkoxy and cyano.

8. The method of claim 1, wherein R$^1$, R$^2$ and R$^3$ are independently selected from hydrogen; halogen; $C_{1-4}$ alkyl, which is optionally substituted with one or more halogen atoms; $C_{1-4}$ alkoxy; $C_{6-10}$ ; aryl; heteroaryl; nitro; amino; and $C_{2-6}$ aliphatic acyl, which may be optionally substituted with one or more halogen atoms; provided that at least one of R$^1$, R$^2$ and R$^3$ are other than hydrogen.

9. The method of claim 1, wherein R$^1$, R$^2$ and R$^3$ are independently selected from hydrogen, chorine, bromine, methyl, ethyl, methoxy, ethoxy, acetyl, chioroacetyl, phenyl, morpholino, nitro, amino, and bromoacetyl, provided that at least one of R$^1$, R$^2$ and R$^3$ is other than hydrogen.

10. The method of claim 1, wherein R$^1$, R$^2$ and R$^3$ are independently selected from hydrogen, chioro, bromo, iodo, methyl, methoxy, acetyl, phenyl, morpholino, nitro, amino, and chioroacetyl, provided that at least one of R$^1$, R$^2$ and R$^3$ is other than hydrogen.

11. The method of claim 1, wherein the compound is selected from the following table:

| comp. | —X— | COCY$^1$Y$^2$Y$^3$ | R$^1$ | R$^2$ | R$^3$ |
|---|---|---|---|---|---|
| 1 | —S— | 3-COCH$_2$Cl | 2-Br | 4-Cl | 5-Cl |
| 2 | —S— | 2-COCH$_2$Cl | 4-Cl | 5-Cl | H |
| 3 | —S— | 2-COCH$_2$Cl | 4-Br | H | H |
| 4 | —S— | 3-COCH$_2$Cl | 4-Cl | H | H |
| 5 | —S— | 3-COCH$_2$Cl | 2-Br | 4-Br | 5-Br |
| 6 | —S— | 3-COCH$_2$Cl | 2-Cl | 5-Cl | H |
| 7 | —S— | 2-COCH$_2$Cl | 5-Cl | H | H |
| 8 | —S— | 2-COCH$_2$Cl | 5-Br | H | H |
| 9 | —S— | 2-COCH$_2$Cl | 4-COCH$_2$Cl | H | H |
| 10 | —S— | 2-COCH$_2$Cl | H | H | H |
| 11 | —S— | 2-COCH$_2$Cl | 4-COCH$_2$Cl | 5-CH$_3$ | H |
| 12 | —S— | 2-COCH$_2$Cl | 5-CH$_3$ | H | H |
| 13 | —S— | 3-COCH$_2$Cl | 2-CH$_3$ | 5-CH$_3$ | H |
| 14 | —S— | 2-COCH$_2$Cl | 4-Br | 5-Br | H |
| 15 | —S— | 2-COCH$_2$Cl | 3-Br | 4-Br | H |
| 16 | —S— | 2-COCH$_2$Cl | 3-CH$_3$ | 4-COCH$_2$Cl | H |
| 17 | —S— | 2-COCH$_2$Cl | 4-CH$_3$ | H | H |
| 18 | —S— | 2-COCH$_2$Cl | 3-CH$_3$ | H | H |
| 19 | —S— | 2-COCH$_2$Cl | 5-COCH$_3$ | H | H |
| 20 | —S— | 2-COCH$_2$Cl | 4-COCH$_3$ | H | H |
| 21 | —S— | 2-COCH$_2$Br | 3-Br | 4-Br | H |
| 22 | —S— | 2-COCH$_2$Br | 4-Br | 5-Br | H |
| 23 | —S— | 2-COCH$_2$Br | 5-Br | H | H |

12. The method of claim 1, wherein the disease is Alzheimer's disease.

13. The method of claim 1, wherein the disease is non-dependent insulin diabetes mellitus.

14. The method of claim 1, wherein the disease is a hyperproliferative disease.

15. The method of claim 14, wherein the hyperproliferative disease is selected from cancer, displasias and metaplasia of different tissues, psoriasis, arteriosclerosis, or restenosis.

16. The method of claim 1, wherein the subject is a human.

* * * * *